United States Patent
Cao et al.

(10) Patent No.: US 9,434,949 B2
(45) Date of Patent: Sep. 6, 2016

(54) USES OF THE HUMAN ZFX GENE AND DRUGS ASSOCIATED WITH SAME

(75) Inventors: Yueqiong Cao, Shanghai (CN); Dalong Lv, Shanghai (CN); Xiangying Zhu, Shanghai (CN); Haixiong Han, Shanghai (CN); Honghua Qu, Shanghai (CN); Yangsheng Jin, Shanghai (CN)

(73) Assignee: SHANGHAI GENECHEM CO., LTD., Shanghai (CN)

( * ) Notice: Subject to any disclaimer, the term of this patent is extended or adjusted under 35 U.S.C. 154(b) by 116 days.

(21) Appl. No.: 14/239,120

(22) PCT Filed: Aug. 16, 2011

(86) PCT No.: PCT/CN2011/078482
§ 371 (c)(1),
(2), (4) Date: May 27, 2014

(87) PCT Pub. No.: WO2013/023361
PCT Pub. Date: Feb. 21, 2013

(65) Prior Publication Data
US 2014/0275219 A1    Sep. 18, 2014

(51) Int. Cl.
*A61K 48/00* (2006.01)
*C12N 15/113* (2010.01)
*A61K 45/06* (2006.01)
*A61K 31/7105* (2006.01)
*A61K 31/713* (2006.01)

(52) U.S. Cl.
CPC ......... *C12N 15/1135* (2013.01); *A61K 31/713* (2013.01); *A61K 31/7105* (2013.01); *A61K 45/06* (2013.01); *C12N 15/113* (2013.01); *C12N 2310/14* (2013.01); *C12N 2740/15043* (2013.01)

(58) Field of Classification Search
None
See application file for complete search history.

(56) References Cited

U.S. PATENT DOCUMENTS 5,759,772 A    6/1998 Kirkpatrick et al.

FOREIGN PATENT DOCUMENTS

CN    102277434    12/2011

OTHER PUBLICATIONS

Cellot and Sauvageau, "Zfx: at the crossroads of survival and self-renewal," Cell (2007) 129(2):239-241.
GenBank Database Accession No. NM_003410, retrieved from the Internet Jun. 24, 2014, 4 pages.
Guo et al., "Effect of Zfx gene on self-renewal of stem cells," Chemistry of Life (2008) 28(3):245-247, ISSN 1000-1336.
International Preliminary Report on Patentability and Written Opinion for PCT/CN2011/078482 issued Feb. 18, 2014, 15 pages (English language translation).
International Search Report for PCT/CN2011/078482, mailed May 17, 2012, 13 pages (English language translation attached).
North et al., "Comparison of ZFY and ZFX gene structure and analysis of alternative 3' untranslated regions of ZFY," Nucleic Acids Res. (1991) 19(10):2579-2586.
Oyanagi et al., "Expression of LUN gene that encodes a novel RING finger protein is correlated with development and progression of non-small cell lung cancer," Lung Cancer (2004) 46:21-28.
Palmer et al., "Comparison of human ZFY and ZFX transcripts," Proc Natl Acad Sci USA (1990) 87(5):1681-1685.
Poloumienko et al., "Cloning and comparative analysis of the bovine, porcine, and equine sex chromosome genes ZFX and ZFY," Genome (2004) 47(1):74-83.
Ramalho-Santos et al., "'Stemness': transcriptional profiling of embryonic and adult stem cells," Science (2002) 298(5593):597-600.
Rao et al., "The expression of zinc finger protein x-linked in human gliomas," Chinese J Neuro-Oncol (2009) 7(4):236-240.
Schneider-Gadicke et al., "ZFX has a gene structure similar to ZFY, the putative human sex determinant, and escapes X inactivation," Cell (1989) 57(7):1247-1258.
Uprichard, "The therapeutic potential of RNA interference," FEBS Lett. (2005) 579(26):5996-6007.
Vendrell et al., "A20/TNFAIP3, a new estrogen-regulated gene that confers tamoxifen resistance in breast cancer cells," Oncogene (2007) 26(32):4656-4667.
Witkiewicz-Kucharczyk and Bal, "Damage of zinc fingers in DNA repair proteins, a novel molecular mechanism in carcinogenesis," Toxicol Lett (2006) 162(1):29-42.
Yajima et al., "Zinc finger protein 28 as a novel melanoma-related molecule," J Dermatol Sci (2009) 55(1):68-70.
Zamore et al., "RNAi: double-stranded RNA directs the ATP-dependent cleavage of mRNA at 21 to 23 nucleotide intervals," Cell (2000) 101(1):25-33.

*Primary Examiner* — Kimberly Chong
(74) *Attorney, Agent, or Firm* — Morrison & Foerster LLP

(57) ABSTRACT

The present invention discloses uses of the human ZFX gene and drugs associated therewith. Also disclosed are uses of the human ZFX gene in tumor treatment, tumor diagnosis, and drug preparation. Further disclosed are small interfering RNA (siRNA), and nucleic acid and lentivirus encoding the siRNA to the human ZFX gene and uses thereof. The siRNA and nucleic acid and lentivirus encoding the siRNA provided by the present invention can specifically inhibit the expression of human ZFX gene. Lentiviruses in particular can efficiently infect target cells, inhibit ZFX expression in target cells, and inhibit the growth of tumor cells, thus promote tumor apoptosis and have great significance in tumor treatment.

27 Claims, 7 Drawing Sheets

(a)

(b)

SEQUENCE LISTING

```
<160> NUMBER OF SEQ ID NOS: 50

<210> SEQ ID NO 1
<211> LENGTH: 21
<212> TYPE: DNA
<213> ORGANISM: Homo sapiens

<400> SEQUENCE: 1
aacaggagct gatggtacac a                                              21

<210> SEQ ID NO 2
<211> LENGTH: 21
<212> TYPE: DNA
<213> ORGANISM: Homo sapiens

<400> SEQUENCE: 2
caggagctga tggtacacac a                                              21

<210> SEQ ID NO 3
<211> LENGTH: 21
<212> TYPE: DNA
<213> ORGANISM: Homo sapiens

<400> SEQUENCE: 3
gtggaagtac aagaaactgt t                                              21

<210> SEQ ID NO 4
<211> LENGTH: 21
<212> TYPE: DNA
<213> ORGANISM: Homo sapiens

<400> SEQUENCE: 4
atgttattga ggacgttgtt a                                              21
```

```
<210> SEQ ID NO 5
<211> LENGTH: 21
<212> TYPE: DNA
<213> ORGANISM: Homo sapiens

<400> SEQUENCE: 5
atggaagaag cagatgtgtc t                                              21

<210> SEQ ID NO 6
<211> LENGTH: 21
<212> TYPE: DNA
<213> ORGANISM: Homo sapiens

<400> SEQUENCE: 6
tacttcagcc tcaatgtcta t                                              21

<210> SEQ ID NO 7
<211> LENGTH: 21
<212> TYPE: DNA
<213> ORGANISM: Homo sapiens

<400> SEQUENCE: 7
cgggtgattc tatacatgtg t                                              21

<210> SEQ ID NO 8
<211> LENGTH: 21
<212> TYPE: DNA
<213> ORGANISM: Homo sapiens

<400> SEQUENCE: 8
gtgtctgacg ttggacatgt t                                              21

<210> SEQ ID NO 9
<211> LENGTH: 21
<212> TYPE: DNA
<213> ORGANISM: Homo sapiens

<400> SEQUENCE: 9
gacgttggac atgttggaca t                                              21

<210> SEQ ID NO 10
<211> LENGTH: 21
<212> TYPE: DNA
<213> ORGANISM: Homo sapiens

<400> SEQUENCE: 10
tggacatgtt ggacatgttg a                                              21

<210> SEQ ID NO 11
<211> LENGTH: 21
<212> TYPE: DNA
<213> ORGANISM: Homo sapiens

<400> SEQUENCE: 11
tagtggaagc agaaattgtc a                                              21

<210> SEQ ID NO 12
<211> LENGTH: 21
<212> TYPE: DNA
<213> ORGANISM: Homo sapiens

<400> SEQUENCE: 12
gtggaagcag aaattgtcac t                                              21
```

<210> SEQ ID NO 13
<211> LENGTH: 21
<212> TYPE: DNA
<213> ORGANISM: Homo sapiens

<400> SEQUENCE: 13
ttgtcactga tcctctgact a                                              21

<210> SEQ ID NO 14
<211> LENGTH: 21
<212> TYPE: DNA
<213> ORGANISM: Homo sapiens

<400> SEQUENCE: 14
accgacgtag tttcagaaga a                                              21

<210> SEQ ID NO 15
<211> LENGTH: 21
<212> TYPE: DNA
<213> ORGANISM: Homo sapiens

<400> SEQUENCE: 15
taccttatga tttccttgga t                                              21

<210> SEQ ID NO 16
<211> LENGTH: 21
<212> TYPE: DNA
<213> ORGANISM: Homo sapiens

<400> SEQUENCE: 16
atggacacag agtcggaaat t                                              21

<210> SEQ ID NO 17
<211> LENGTH: 21
<212> TYPE: DNA
<213> ORGANISM: Homo sapiens

<400> SEQUENCE: 17
gacacagagt cggaaattga t                                              21

<210> SEQ ID NO 18
<211> LENGTH: 21
<212> TYPE: DNA
<213> ORGANISM: Homo sapiens

<400> SEQUENCE: 18
gagtcggaaa ttgatccttg t                                              21

<210> SEQ ID NO 19
<211> LENGTH: 21
<212> TYPE: DNA
<213> ORGANISM: Homo sapiens

<400> SEQUENCE: 19
gtcggaaatt gatccttgta a                                              21

<210> SEQ ID NO 20
<211> LENGTH: 21
<212> TYPE: DNA
<213> ORGANISM: Homo sapiens

<400> SEQUENCE: 20

-continued

```
gagagtgagc ctgagaatga t                                           21

<210> SEQ ID NO 21
<211> LENGTH: 21
<212> TYPE: DNA
<213> ORGANISM: Homo sapiens

<400> SEQUENCE: 21
agcaaatgga tgacaatgaa a                                           21

<210> SEQ ID NO 22
<211> LENGTH: 21
<212> TYPE: DNA
<213> ORGANISM: Homo sapiens

<400> SEQUENCE: 22
atggatgaca atgaaatcaa a                                           21

<210> SEQ ID NO 23
<211> LENGTH: 21
<212> TYPE: DNA
<213> ORGANISM: Homo sapiens

<400> SEQUENCE: 23
ctgtgaatac gagacagctg a                                           21

<210> SEQ ID NO 24
<211> LENGTH: 21
<212> TYPE: DNA
<213> ORGANISM: Homo sapiens

<400> SEQUENCE: 24
taccaatgcc agtactgcga a                                           21

<210> SEQ ID NO 25
<211> LENGTH: 21
<212> TYPE: DNA
<213> ORGANISM: Homo sapiens

<400> SEQUENCE: 25
gtcttctgac tttctcggat a                                           21

<210> SEQ ID NO 26
<211> LENGTH: 21
<212> TYPE: DNA
<213> ORGANISM: Homo sapiens

<400> SEQUENCE: 26
taccaaagag gtgcagcaac a                                           21

<210> SEQ ID NO 27
<211> LENGTH: 21
<212> TYPE: DNA
<213> ORGANISM: Homo sapiens

<400> SEQUENCE: 27
atgctcttat ccaccaagaa a                                           21

<210> SEQ ID NO 28
<211> LENGTH: 21
<212> TYPE: DNA
<213> ORGANISM: Homo sapiens

<400> SEQUENCE: 28
```

-continued

```
gcgaccacaa gagttcgaac t                                              21

<210> SEQ ID NO 29
<211> LENGTH: 21
<212> TYPE: DNA
<213> ORGANISM: Homo sapiens

<400> SEQUENCE: 29
gaccacaaga gttcgaactc a                                              21

<210> SEQ ID NO 30
<211> LENGTH: 21
<212> TYPE: DNA
<213> ORGANISM: Homo sapiens

<400> SEQUENCE: 30
accacaagag ttcgaactca a                                              21

<210> SEQ ID NO 31
<211> LENGTH: 21
<212> TYPE: DNA
<213> ORGANISM: Homo sapiens

<400> SEQUENCE: 31
gtgatttgaa acgacacata a                                              21

<210> SEQ ID NO 32
<211> LENGTH: 21
<212> TYPE: DNA
<213> ORGANISM: Homo sapiens

<400> SEQUENCE: 32
ttcagttcac acgaaagact a                                              21

<210> SEQ ID NO 33
<211> LENGTH: 21
<212> TYPE: DNA
<213> ORGANISM: Homo sapiens

<400> SEQUENCE: 33
aagtgtgaca tgtgtgataa a                                              21

<210> SEQ ID NO 34
<211> LENGTH: 21
<212> TYPE: DNA
<213> ORGANISM: Homo sapiens

<400> SEQUENCE: 34
taggtgcaag agatgtagaa a                                              21

<210> SEQ ID NO 35
<211> LENGTH: 21
<212> TYPE: DNA
<213> ORGANISM: Homo sapiens

<400> SEQUENCE: 35
aggcaacaga gtgagcttaa a                                              21

<210> SEQ ID NO 36
<211> LENGTH: 21
<212> TYPE: DNA
<213> ORGANISM: Homo sapiens
```

```
<400> SEQUENCE: 36
cacagtggca ggaaagtgta t                                              21

<210> SEQ ID NO 37
<211> LENGTH: 21
<212> TYPE: DNA
<213> ORGANISM: Homo sapiens

<400> SEQUENCE: 37
cagtggcagg aaagtgtatc a                                              21

<210> SEQ ID NO 38
<211> LENGTH: 21
<212> TYPE: DNA
<213> ORGANISM: Homo sapiens

<400> SEQUENCE: 38
ggcaggaaag tgtatcagtg t                                              21

<210> SEQ ID NO 39
<211> LENGTH: 21
<212> TYPE: DNA
<213> ORGANISM: Homo sapiens

<400> SEQUENCE: 39
aaccagcaca taatgcgaca t                                              21

<210> SEQ ID NO 40
<211> LENGTH: 21
<212> TYPE: DNA
<213> ORGANISM: Homo sapiens

<400> SEQUENCE: 40
cagcacataa tgcgacatca t                                              21

<210> SEQ ID NO 41
<211> LENGTH: 21
<212> TYPE: DNA
<213> ORGANISM: Homo sapiens

<400> SEQUENCE: 41
agcacataat gcgacatcat a                                              21

<210> SEQ ID NO 42
<211> LENGTH: 21
<212> TYPE: DNA
<213> ORGANISM: Homo sapiens

<400> SEQUENCE: 42
cacataatgc gacatcataa a                                              21

<210> SEQ ID NO 43
<211> LENGTH: 51
<212> TYPE: RNA
<213> ORGANISM: Artificial Sequence
<220> FEATURE:
<223> OTHER INFORMATION: Synthetic shRNA

<400> SEQUENCE: 43
gucggaaauu gauccuugua auucaagaga uuacaaggau caauuuccga c             51

<210> SEQ ID NO 44
<211> LENGTH: 24
<212> TYPE: DNA
<213> ORGANISM: Artificial Sequence
```

```
<220> FEATURE:
<223> OTHER INFORMATION: primer

<400> SEQUENCE: 44
cctatttccc atgattcctt cata                                              24

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
gtaatacggt tatccacgcg                                                   20

<210> SEQ ID NO 46
<211> LENGTH: 19
<212> TYPE: DNA
<213> ORGANISM: Artificial Sequence
<220> FEATURE:
<223> OTHER INFORMATION: primer

<400> SEQUENCE: 46
ttctccgaac gtgtcacgt                                                    19

<210> SEQ ID NO 47
<211> LENGTH: 19
<212> TYPE: DNA
<213> ORGANISM: Artificial Sequence
<220> FEATURE:
<223> OTHER INFORMATION: primer

<400> SEQUENCE: 47
ggcagtccac agcaagaac                                                    19

<210> SEQ ID NO 48
<211> LENGTH: 23
<212> TYPE: DNA
<213> ORGANISM: Artificial Sequence
<220> FEATURE:
<223> OTHER INFORMATION: primer

<400> SEQUENCE: 48
ttggtatccg agaaagtcag aag                                               23

<210> SEQ ID NO 49
<211> LENGTH: 21
<212> TYPE: DNA
<213> ORGANISM: Artificial Sequence
<220> FEATURE:
<223> OTHER INFORMATION: primer

<400> SEQUENCE: 49
tgacttcaac agcgacaccc a                                                 21

<210> SEQ ID NO 50
<211> LENGTH: 21
<212> TYPE: DNA
<213> ORGANISM: Artificial Sequence
<220> FEATURE:
<223> OTHER INFORMATION: primer

<400> SEQUENCE: 50
caccctgttg ctgtagccaa a                                                 21
```

US 9,434,949 B2

USES OF THE HUMAN ZFX GENE AND DRUGS ASSOCIATED WITH SAME

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 699312000100SeqList.txt, date recorded: Jan. 5, 2016, size: 7,320 bytes).

TECHNICAL FIELD

The present invention relates to the field of biotechnology. In particular, it relates to the uses of the human ZFX gene and drugs associated with same.

BACKGROUND ART

Ribonucleic acid interference (RNA interference, RNAi) refers to the following phenomenon: after double-stranded RNA (dsRNA) homologous to a certain sequence in an endogenous mRNA coding region is introduced into a cell, the mRNA undergoes specific degradation, with the result that the gene is silenced. Research has shown that double-stranded RNA of length 21-23 nt can specifically induce RNAi at the transcription or post-transcription level (Tuschl et al., *Cell* (2000) 101: 25-33). Tumors are major diseases that threaten human health. In spite of chemotherapy, radiotherapy, and combination therapy, the five-year survival rate for tumor patients is still quite low. New avenues in tumor treatment could be opened up if the genes relating to the onset and progress of tumors could be subjected to RNA interference. In recent years, RNAi has become an effective strategy for tumor gene therapy. The use of RNAi techniques can inhibit the expression of oncogenes, mutated tumor suppressor genes, cell cycle-related genes, and anti-apoptosis genes and thereby inhibit the occurrence and development of tumors (Uprichard, *FEBS Lett.* (2005) 579:5996-6007).

The zinc finger protein family is the largest protein family in human and is the most common structural element in nucleic acid identification. Research has found that 1% of human genes belong to the zinc finger protein gene family. Zinc finger proteins can regulate gene expression by targeting gene promoter regions, and play an important role in the growth, proliferation, and differentiation of histocytes. Their abnormal expression may cause many diseases, including malignant tumors (Yajima et al., *J Dermatol Sci.* (2009) 55:68-70; Oyanagi et al., *Lung Cancer* (2004) 46:21-28; Witkiewicz-Kucharczyk & Bal, *Toxicol. Lett.* (2006) 162: 29-42; Vendrell et al., *Oncogene* (2007) 26:4656-4667).

The ZFY (zinc finger-Y) gene family is a highly conserved gene family among vertebrates. It is now known that the ZFY gene family includes three members: the ZFX, ZFY, and ZFA genes. Their molecular structures are highly similar (North et al., *Nucleic Acids Res.* (1991) 19:2579-2586). Generally, all mammals have ZFX and ZFY genes, with the ZFX gene being located on the X chromosome and the ZFY gene being located on the Y chromosome (Palmer et al., *Proc. Natl. Acad. Sci. USA* (1990) 87:1681-1685). Extensive research has verified that the ZFY gene family is related to the sex-determination of animals. In-depth studies have shown that the ZFY gene family may be related to testicular development and may decide the sexual development of animals (Schneider-Gadicke et al., *Cell* (1989) 57:1247-1258).

The full-length ZFX protein contains an acidic transcriptional activation domain (AD), a nuclear localization sequence (NLS), and a DNA binding domain (DBD) with 13 $Cys_2His_2$ (C2H2) zinc finger structures (Poloumienko et al., *Genome* (2004) 47: 74-83). In mammalian cells, the C2H2 zinc finger structure is one of the most common protein structures and has a potential transcription-regulation function. So far, more than 800 proteins have been found to have such a zinc finger structure, and the majority has been verified as having important physiological functions. In recent years, scientists have discovered, in the course of researching the gene expression processes of different stem cells, that the ZFX gene is highly expressed within several types of stem cells (Ramalho-Santos et al., *Science* (2002) 298:597-600). It has also been reported that the ZFX gene has the function of regulating stem cell self-renewal (Cellot & Sauvageau, *Cell* (2007) 129:239-241). However, there have been no reports so far on the ZFX gene in tumor-related fields.

SUMMARY OF THE INVENTION

The present invention relates to uses of the human ZFX gene and drugs associated with same.

In one aspect, the present invention provides methods of treating tumors, by inhibiting the expression level or activity of the ZFX gene to inhibit or attenuate the growth, proliferation, differentiation and/or survival of a tumor cell.

In some embodiment, the so-called tumor may be any kind of tumors of which growth, proliferation, differentiation and/or survival are associated with the expression or activity of the ZFX gene, further the tumor may be malignant tumors, and even further the tumor may be selected from the group consisting of laryngeal cancer, lung cancer, stomach cancer, liver cancer, mammary gland cancer and glioma.

In some embodiment, the so-called methods of treating tumors refers to methods which comprise administering to the subject a molecule that specifically inhibits or lower the expression level of a ZFX gene.

Further, in some embodiment, the so-called molecule specifically inhibits or lower the expression level of the ZFX gene, may be an siRNA (small interfering RNA) which could specifically silence the expression of a ZFX gene, and thus specifically silencing the expression of endogenous ZFX genes in tumor cells.

Further, in some embodiments, the human ZFX gene siRNA targeted the sequence which comprises a sequence set forth as anyone in SEQ ID NOs:1-42 for specifically silencing the human ZFX genes expression.

Even further, in some embodiments, the so-called "the human ZFX gene siRNA targeted the sequence which comprises a sequence set forth as anyone in SEQ ID NOs:1-42 for specifically silencing the human ZFX genes expression" means that, the siRNA could specifically bind the mRNA which is encoded by a sequence set forth as anyone in SEQ ID NOs: 1-42 and could specifically silence the expression of a ZFX gene.

In some embodiments, the siRNA, which could specifically silence the expression of a ZFX gene, is expressed via a lentivirus vector. In detail, in some embodiments, the procedure include steps of firstly cloning the DNA segment encoding the siRNA of human ZFX gene into a lentivirus vector to obtain a human ZFX gene interference lentivirus vector, then packaging the vector with a lentivirus to obtain infectious lentivirus particles, infecting tumor cells and finally expressing the above mentioned siRNA.

The so-called human ZFX gene interference lentivirus vector is obtained by cloning the DNA segments encoding the human ZFX gene siRNA into a lentivirus vector, and the human ZFX gene interference lentivirus vector could produce human ZFX gene siRNA.

In some embodiments, the lentivirus vector may be selected from the group consisting of pLKO.1-puro, pLKO.1-CMV-tGFP, pLKO.1-puro-CMV-tGFP, pLKO.1-CMV-Neo, pLKO.1-Neo, pLKO.1-Neo-CMV-tGFP, pLKO.1-puro-CMV-TagCFP, pLKO.1-puro-CMV-TagYFP, pLKO.1-puro-CMV-TagRFP, pLKO.1-puro-CMV-TagFP635, pLKO.1-puro-UbC-TurboGFP, pLKO.1-puro-UbC-TagFP635, pLKO-puro-IPTG-1xLacO, pLKO-puro-IPTG-3xLacO, pLP1, pLP2, pLP/VSV-G, pENTR/U6, pLenti6/BLOCK-iT-DEST, pLenti6-GW/U6-laminshrna, pcDNA1.2/V5-GW/lacZ, pLenti6.2/N-Lumio/V5-DEST, pGCSIL-GFP and pLenti6.2/N-Lumio/V5-GW/lacZ. In the embodiment of the present invention, pGCSIL-GFP was illustrated as vector in detail.

The infectious lentivirus particles could be obtained by means of packaging the lentivirus vectors with the help of lentivirus packaging plasmid and certain cell lines.

The method disclosed by the present invention for inhibiting or attenuating the growth, proliferation, differentiation and/or survival of a tumor cell, e.g., a tumor cell in a subject, which method comprises administering to the tumor cell a molecule that specifically inhibits transcription or translation of a ZFX gene, or expression or activity of a ZFX protein, thereby inhibiting the growth, proliferation, differentiation and/or survival of the tumor cell.

In some embodiments, the molecule specifically inhibits the translation of the ZFX gene. In some embodiments, the molecule may comprise a nucleic acid, a carbohydrate, a fat, a small molecule, a polypeptide or a peptide, wherein the nucleic acid may comprise an antisense oligonucleotide, a double stranded RNA (dsRNA), a ribozyme, an RNase III-prepared short interfering RNA (esiRNA) or a vector-expressed short hairpin RNAs (shRNA). In some embodiments, the dsRNA, ribozyme, esiRNA or shRNA may comprise a subsequence of a promoter or a message of the ZFX gene. In some embodiments, the dsRNA may be an siRNA, wherein the siRNA may comprise a sense strand, which may comprise a nucleotide sequence substantially identical to a target sequence in the ZFX gene, and an antisense strand, wherein the sense and antisense strands form an RNA duplex.

In some embodiments, the ZFX gene may be from human. In some embodiments, the target sequence in the ZFX gene may comprise a sequence set forth in SEQ ID NOs: 1-42.

In some embodiments, the tumor may be selected from the group consisting of laryngeal cancer, lung cancer, stomach cancer, liver cancer, mammary gland cancer and glioma. In some embodiments, the growth of the tumor cell may be associated with the expression or activity of the ZFX protein.

In some embodiments, in the method of so-called "inhibiting the growth, proliferation, differentiation and/or survival of the tumor cell", the molecule may be administered at a level sufficient to lower the transcription or translation of the ZFX gene, or the expression or activity of the ZFX protein. In some embodiments, the expression of the ZFX gene may be attenuated by at least about 50%, 80%, 90%, 95% or 99%.

In the second aspect, the present invention provides usage of human ZFX gene for the preparation or screening of pharmaceutical composition for preventing or treating tumors, or usage of human ZFX gene for the preparation or screening of pharmaceutical composition for detecting tumor cells.

The above described term of "usage of human ZFX gene for the preparation or screening of pharmaceutical composition for preventing or treating tumor" includes two parts: firstly, the usage of human ZFX gene, being as the target site mediated by the composition or preparation focus on the tumor cells, in the preparation of pharmaceutical composition for preventing or treating tumors; and secondly, the usage of human ZFX gene, being as the target site mediated by the composition or preparation focus on the tumor cells, in the screening of pharmaceutical composition for preventing or treating tumors.

The above described term of "the human ZFX gene being as the target site mediated by the composition or preparation focus on the tumor cells" means that, the human ZFX gene being as siRNA target site during the RNA interference process which is mediated by the pharmaceutical composition specifically on tumor cells, thus attenuating the expression of a human ZFX gene in a tumor cell.

The above described term of "usage of human ZFX gene, being as the target site in the RNA interference mediated by the composition or preparation focus on the tumor cells, in the screening of pharmaceutical composition for preventing or treating tumors" means that, screening the specific pharmaceutical composition or preparation by using human ZFX as the target site to find out those pharmaceutical composition which could specifically attenuate or increase the expression of human ZFX gene as certain drugs for treating tumors. For example, the above mentioned human ZFX gene siRNA is obtained after screening by using human ZFX gene as the target site, and the obtained ZFX gene siRNA could be used in preparing the pharmaceutical composition which could specifically inhibit tumor cell proliferation, such as antibody drugs, small molecule drugs and so on, which could also use ZFX gene as target site.

The above described term of "usage of human ZFX gene for the preparation of pharmaceutical composition for detecting tumor cells" means that, the expression level of a ZFX gene product is used as tumor diagnosis indicator for the preparation of pharmaceutical composition for detecting tumor cells.

In some embodiments, the so-called tumor may be any kind of tumor of which the growth may be associated with the expression or activity of the ZFX gene. For example, the tumor may be selected from the group consisting of laryngeal cancer, lung cancer, stomach cancer, liver cancer, mammary gland cancer and glioma.

The pharmaceutical composition for treating or preventing tumors may be selected from the group consisting of antibody drugs, small molecule drugs and nucleotide drugs.

Further, the pharmaceutical composition for treating or preventing tumors could attenuate the expression of a ZFX gene, thereby inhibiting the growth, proliferation, differentiation and/or survival of the tumor cell.

In the third aspect, the present invention provides an isolated human ZFX gene siRNA target sequence which comprises a sequence set forth in SEQ ID NOs:1-42.

The isolated human ZFX gene siRNA target sequence may be used in the screening or preparation of human ZFX gene siRNA.

In the fourth aspect, the present invention provides a human ZFX gene siRNA which could specifically silence the human ZFX gene expression.

The human ZFX gene siRNA targeted the sequence which comprises a sequence set forth as anyone in SEQ ID NOs:1-42 for specifically silencing the human ZFX gene expression.

Further, the human ZFX siRNA includes a sense RNA fragment and an antisense RNA fragment which is complementary to the sense RNA fragment. The sense RNA fragment comprises a sequence set forth as anyone in SEQ ID NOs:1-42.

The sense RNA fragment and the antisense RNA fragment may be located on two different RNA strands or located on a same RNA strand.

The sense and antisense RNA fragments both have about 15-27 consecutive nucleotides; preferably 19-23 consecutive nucleotides, and most preferably 19, or 20 or 21 consecutive nucleotides.

Further, the human ZFX gene siRNA is a single-stranded hairpin RNA molecule which comprises a sense RNA fragment and an antisense RNA fragment, the sense RNA fragment and the antisense RNA fragment are separated by a loop fragment, wherein the antisense RNA fragment is complementary to the sense RNA fragment and the sense RNA fragment comprises a sequence set forth in SEQ ID NOs:1-42.

The loop fragments may comprise a sequence which have 6 or 9 bases; preferably, the loop fragments may comprise a sequence selected from the group consisting of UUCAAGAGA, AUG, CCC, UUCG, CCACC, CTCGAG, AAGCUU and CCACACC. In the embodiment of the present invention, UUCAAGAGA was illustrated as loop fragment in detail.

In some embodiments, the human siRNA may comprise the sequence set forth in SEQ ID NO:43 (GUCG-GAAAUUGAUCCUUGUAAUUCAAGAGAUUA-CAAGGAUCAAUUUCCGAC).

In the fifth aspect, the present invention provides a human ZFX interference nucleic acid construct that comprises a gene fragment encoding the above-described human ZFX siRNA. The human ZFX interference nucleic acid construct expresses the above-described human ZFX siRNA.

The human ZFX interference nucleic acid construct may be constructed by means of cloning the above-described gene fragment encoding the above-described human ZFX siRNA into a known vector.

Further, the human ZFX interference nucleic acid construct is a human ZFX interference lentivirus vector, which is obtained by cloning the gene fragment encoding the human ZFX siRNA into a lentivirus vector to produce human ZFX siRNA.

The lentivirus vector may be selected from the group consisting of pLKO.1-puro, pLKO.1-CMV-tGFP, pLKO.1-puro-CMV-tGFP, pLKO.1-CMV-Neo, pLKO.1-Neo, pLKO.1-Neo-CMV-tGFP, pLKO.1-puro-CMV-TagCFP, pLKO.1-puro-CMV-TagYFP, pLKO.1-puro-CMV-TagRFP, pLKO.1-puro-CMV-TagFP635, pLKO.1-puro-UbC-TurboGFP, pLKO.1-puro-UbC-TagFP635, pLKO-puro-IPTG-1xLacO, pLKO-puro-IPTG-3xLacO, pLP1, pLP2, pLP/VSV-G, pENTR/U6, pLenti6/BLOCK-iT-DEST, pLenti6-GW/U6-laminshrna, pcDNA1.2/V5-GW/lacZ, pLenti6.2/N-Lumio/V5-DEST, pGCSIL-GFP and pLenti6.2/N-Lumio/V5-GW/lacZ.

In the embodiment of the present invention, pGCSIL-GFP was illustrated as lentivirus vector in detail for obtaining the human ZFX interference nucleic acid construct which is named as pGCSIL-GFP-ZFX-siRNA-1.

Further, the gene fragment encoding the human ZFX siRNA comprises a sequence set forth as anyone in SEQ ID NOs:1-42 and its complementary sequence.

The human ZFX gene siRNA could be used for inhibiting or attenuating the growth, proliferation, differentiation and/or survival of a tumor cell, and further be used in preparation of pharmaceutical composition or preparation for treating or detecting tumors. The human ZFX interference nucleic acid construct could be used for producing the human ZFX siRNA.

While used in preparation of pharmaceutical composition for treating tumors, a therapeutically effective amount of human ZFX siRNA is administered to a mammalian subject. The specific dosage should be determined by a skilled physician by considering administration strategy and patient healthy conditions.

In the sixth aspect, the present invention provides a human ZFX interference lentivirus, which is obtained by means of packaging the lentivirus vectors with the help of lentivirus packaging plasmid and certain cell lines. The human ZFX interference lentivirus could infect tumor cells and produce human ZFX siRNA, thus inhibiting the growth and/or proliferation of tumor cells.

In the seventh aspect, the present invention provides a pharmaceutical composition which comprises therapeutically effective amount of human ZFX siRNA or human ZFX interference lentivirus.

Further, the pharmaceutical composition comprises 1-99 wt % of the above-described human ZFX siRNA or human ZFX interference lentivirus, with pharmaceutically acceptable carrier, diluent or excipient.

During preparation of the pharmaceutical composition, the active ingredients are generally mixed with an excipient or are diluted with an excipient or are wrapped in a carrier that can exist in the form of a capsule or a bag. When the excipient acts as a diluent, it can serve as a solid, semi-solid, or liquid medium for the excipient, carrier, or active ingredients. Therefore, the pharmaceutical composition may be in the form of tablets, pills, powder, solution, syrup, or sterile injection solutions. Examples of suitable excipients include lactose, glucose, sucrose, sorbitol, mannitol, starch, microcrystalline cellulose, polyvinyl pyrrolidone, cellulose, and water. Preparations may also include: lubricants, emulsifiers, preservatives (such as methyl and propyl p-hydroxybenzoate), and sweeteners.

In the eighth aspect, the present invention provides an isolated oligonucleotide molecule that attenuates the expression of a ZFX gene in a tumor cell, which comprises:

a) a dsRNA sequence comprising a nucleotide sequence that hybridizes under stringent conditions to the ZFX gene; or b) a DNA sequence comprising a nucleotide sequence that is transcribed in the tumor cell to an shRNA comprising a nucleotide sequence that hybridizes under stringent conditions to the ZFX gene.

The shRNA comprises a first strand and a second strand, wherein the first strand of the dsRNA is substantially identical to about 15-27 consecutive nucleotides of the ZFX gene, and the second strand of the dsRNA is substantially complementary to the first strand. Further, the first strand of the dsRNA is substantially identical to a target sequence in the ZFX gene.

The ZFX gene is from human.

Further, the ZFX gene comprises a sequence set forth in SEQ ID NO:1.

Further, the target sequence in the ZFX gene comprises a sequence set forth in SEQ ID NOs: 1-42.

The shRNA molecule comprises a sense RNA fragment and an antisense RNA fragment, the sense RNA fragment comprises a nucleotide sequence which is substantially identical to a target sequence in the ZFX gene. The sense RNA fragment and the antisense RNA fragment are separated by a loop fragment. Further, the loop fragments comprise a sequence selected from the group consisting of UUCAAGAGA, AUG, CCC, UUCG, CCACC, CTCGAG, AAGCUU and CCACACC. Even further, the shRNA comprises the sequence set forth in SEQ ID NO:43.

The DNA sequence may be contained in a lentivirus vector. In some embodiments, the lentivirus vector may further comprise a promoter sequence. In some embodiments, the lentivirus vector may further comprise a nucleotide sequence encoding a detectable marker in the tumor cell, wherein the detectable marker may be a green fluorescent protein (GFP).

In some embodiments, the lentivirus vector may be selected from the group consisting of pLKO.1-puro, pLKO.1-CMV-tGFP, pLKO.1-puro-CMV-tGFP, pLKO.1-CMV-Neo, pLKO.1-Neo, pLKO.1-Neo-CMV-tGFP, pLKO.1-puro-CMV-TagCFP, pLKO.1-puro-CMV-TagYFP, pLKO.1-puro-CMV-TagRFP, pLKO.1-puro-CMV-TagFP635, pLKO.1-puro-UbC-TurboGFP, pLKO.1-puro-UbC-TagFP635, pLKO-puro-IPTG-1xLacO, pLKO-puro-IPTG-3xLacO, pLP1, pLP2, pLP/VSV-G, pENTR/U6, pLenti6/BLOCK-iT-DEST, pLenti6-GW/U6-laminshrna, pcDNA1.2/V5-GW/lacZ, pLenti6.2/N-Lumio/V5-DEST, pGCSIL-GFP and pLenti6.2/N-Lumio/V5-GW/lacZ.

In the ninth aspect, the present invention provides a cell comprising the above-described isolated oligonucleotide molecule.

Further, the cell is comprised in a non-human whole mammal.

In the tenth aspect, the present invention provides a pharmaceutical composition for preventing or treating tumor, the pharmaceutical composition comprises the above-described isolated oligonucleotide molecule that attenuates expression of a ZFX gene.

Further, the pharmaceutical composition comprises a pharmaceutically acceptable carrier or excipient. During preparation of the pharmaceutical composition, the active ingredients are generally mixed with an excipient or are diluted with an excipient or are wrapped in a carrier that can exist in the form of a capsule or a bag. When the excipient acts as a diluent, it can serve as a solid, semi-solid, or liquid medium for the excipient, carrier, or active ingredients. Therefore, the pharmaceutical composition may be in the form of tablets, pills, powder, solution, syrup, or sterile injection solutions. Examples of suitable excipients include lactose, glucose, sucrose, sorbitol, mannitol, starch, microcrystalline cellulose, polyvinyl pyrrolidone, cellulose, and water. Preparations may also include: lubricants, emulsifiers, preservatives (such as methyl and propyl p-hydroxybenzoate), and sweeteners.

In the eleventh aspect, the present invention provides a method for preventing or treating tumor in a subject, which method comprises administering an effective amount of the above-described pharmaceutical composition for preventing or treating tumor into the subject. The tumor is selected from the group consisting of laryngeal cancer, lung cancer, stomach cancer, liver cancer, mammary gland cancer and glioma.

Further, the growth, proliferation, recurrence and/or metastasis of the tumor may be inhibited. Even further, the growth, proliferation, recurrence and/or metastasis of the tumor may be inhibited by at least 10%, 20%, 30%, 40%, 50%, 60%, 70%, 80%, 90%, 95% or 99%. Preferably, the subject is human.

In the twelfth aspect, the present invention provides an isolated oligonucleotide sequence, which comprises a fragment of a ZFX gene, excluding the full-length nucleotide sequence. In some embodiments, the isolated oligonucleotide sequence may comprise DNA, RNA or a derivative thereof. In some embodiments, the isolated oligonucleotide sequence may be substantially identical to at least 10, 15, 20, 25, 30, 35, 40, 45, or 50 consecutive nucleotides. In some embodiments, the isolated oligonucleotide sequence may comprise the nucleotide sequence set forth in SEQ ID NOs: 1-42.

In the thirteenth aspect, the present invention provides a kit for attenuating the expression of a ZFX gene in a tumor cell, which kit comprises, in a container, an isolated oligonucleotide molecule that attenuates expression of a ZFX gene.

In conclusion, the present invention designs 42 RNAi target sequence on human ZFX gene and construct a corresponding ZFX RNAi vector, wherein the RNAi vector pGCSIL-GFP-ZFX-siRNA with the encoding sequence as set forth in SEQ ID NO.:19 could obviously attenuates expression of a ZFX mRNA and ZFX protein. The lentivirus (simplified as 'Lv') is adopted as gene operation tool to carry the RNAi vector pGCSIL-GFP-ZFX-siRNA into tumor cells, such as human larynx cancer Hep 2 cells, lung cancer 95D cells, stomach cancer AGS cells, liver cancer SMMC-7721 cells, breast cancer MCF-7 cells, and glioma U251 cells, in order to introduce the human ZFX RNAi sequence into those tumor cells effectively and specifically, thus attenuating expression of ZFX gene and inhibiting growth and/or proliferation of the above-described tumor cells. Therefore, the lentiviral-vector-mediated ZFX gene silence is a potential clinic non-operative therapy.

The siRNA or the nucleic acid and/or lentivirus construct which comprises the siRNA fragment could specifically attenuates expression of human ZFX, especially the lentivirus which could effectively infect target cells, efficiently inhibit ZFX expression in target cells, and inhibit the growth of tumor cells, thus promote tumor apoptosis and have great significance in tumor treatment.

EMBODIMENTS

Figure 1:
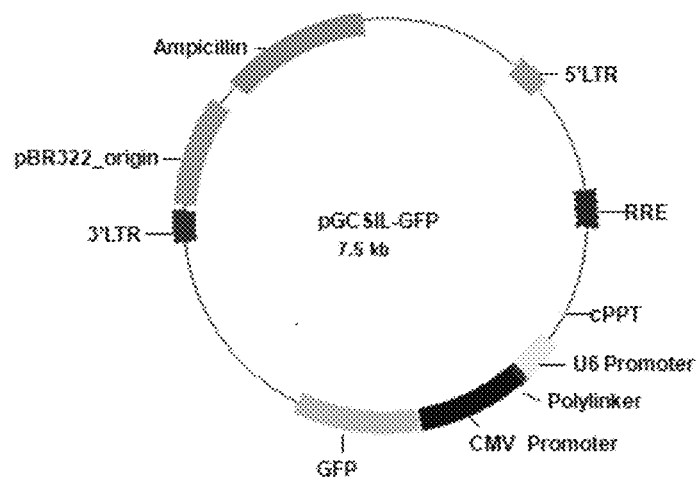
FIG. 1 shows DNA profiles of a pGCSIL-GFP plasmid.

In the present invention, ZFX is regarded as a newfound zinc finger protein which may be involved in the occurrence and development of malignant tumors, according to the related research that the zinc finger protein plays a role in the tumor proliferation, drug resistance and tumor vascularization.

The present invention relates to a series of siRNA sequences, RNA interference vector and RNAi lentivirus targeted human ZFX gene. The human ZFX gene coding sequence (CDS) region was selected as target sites of RNA interference and 10-30 consecutive nucleotides within the target sites, preferably 15-27 consecutive nucleotides and even more preferably 19-23 consecutive nucleotides, was used to design siRNS target. A nucleic acid construct that expresses the above-described siRNA may be constructed by means of gene cloning and packaged with a lentivirus that expresses the above-described siRNA. Cell experiments indicated that the above-described siRNA sequence can specifically silence the expression of endogenous ZFX genes in human tumor cells.

The present invention further relates to the discovery that the use of the RNAi method can, after lowering the expression of the ZFX gene in human tumor cells, effectively inhibit the proliferation of tumor cells. Thus, it is proved that the ZFX gene is an oncogene and thus the ZFX gene can be a target for tumor treatment. Further, a series of siRNA sequences that interfere with human ZFX were synthesized and tested to select the siRNA which can, after lowering the expression of ZFX gene, effectively inhibit the proliferation and growth of tumor cells, such as human larynx cancer Hep 2 cells, lung cancer 95D cells, stomach cancer AGS cells, liver cancer SMMC-7721 cells, breast cancer MCF-7 cells, and glioma U251 cells. The present invention was completed based on the above-described research.

The present invention provides a series of siRNA sequences and constructs a lentivirus which could specifically silence ZFX gene expression. It has been found in the present invention, the siRNA and RNAi lentivirus designed for human ZFX could attenuate the expression of ZFX gene stably and specifically and effectively inhibit the proliferation of human tumor cells. It was demonstrated in the present invention that ZFX gene could promote the growth of tumor cells and possibly be used as target for early diagnosis and treatment of tumors. Besides, it could be an effective approach to inhibit tumor development via silencing the expression of ZFX gene by RNA interference.

The principles of the present invention are as follows.

A human ZFX gene RNAi lentivirus is obtained via the following method: obtaining human ZFX genetic information from Genbank; designing and selecting effective siRNA targets for the human ZFX gene; siRNA sequences targeted the ZFX gene were synthesized as a double-stranded DNA oligonucleotide containing sticky-ended enzyme-cutting sites at both ends; the lentiviral vector was linked to the double-stranded DNA oligo after double enzyme digestion to construct RNAi plasmid expressing the ZFX siRNA sequence; the auxiliary vectors (Packing Mix, Sigma-Aldrich) required for RNAi plasmid and lentiviral packaging were jointly transfected onto human embryo kidney cells 293T to produce recombinant lentiviruses. Thus, lentiviruses that efficiently silence the ZFX gene were produced.

According to the above method, the present invention provides 42 effective siRNA targets for the human ZFX gene as set forth in SEQ ID NOs: 1-42 and constructs lentivirus which specifically mediates RNA interference of the mRNA of human ZFX gene.

At the same time, the present invention also provides a human ZFX gene RNAi lentivirus (ZFX-RNAi) and its preparation and usage.

In the present invention, it has been found that RNAi approach mediated by lentivirus could, after lowering the expression of the ZFX gene in tumor cells, effectively inhibit the proliferation of tumor cells. It has been demonstrated that ZFX gene, as an oncogene which would promote tumor growth and play an important role in growth and proliferation of tumor cells, has been verified as having important physiological functions during the occurrence and development of malignant tumors. Therefore, ZFX gene could be a target during tumor treatment and specific silence of ZFX gene mediated by lentivirus may be a new approach for tumor treatment.

The implementation of the present invention is described below through specific embodiments. The principle and efficacy of the present invention are exemplarily described in the foregoing embodiments, which are not intended to limit the present invention. Those skilled in the art could easily understand other advantages and efficacy of the present invention according to the disclosure of the specification. Other suitable moderate stringency and high stringency hybridization buffers and conditions are well known to those of skill in the art and are described, for example, in Sambrook et al., *Molecular Cloning: A Laboratory Manual,* 3rd ed., (Science Press, BeiJing. 2002), or the protocols provided by the manufacturers.

EXAMPLE 1

Preparation of RNAi Lentivirus Directed at Human ZFX Gene

1. Selecting Effective siRNA Targes for Human ZFX Gene

Human ZFX (NM_003410.2) genetic information was obtained from Genbank. Genechem™ (Shanghai Genechem Co., Ltd.) was used to design effective siRNA targets for the human ZFX gene. In the human ZFX gene coding sequence (CDS) region, 21 by sequences starting with every other base were determined. Table 1 lists the 42 effective siRNA target sequences for the human ZFX gene.

TABLE 1 siRNA target sequences of the human ZFX

| SEQ ID NO | Target Sequence | Start site |
| --- | --- | --- |
| 1 | aacaggagctgatggtacaca | 361 |
| 2 | caggagctgatggtacacaca | 363 |

TABLE 1-continued siRNA target sequences of the human ZFX

| SEQ ID NO | Target Sequence | Start site |
|---|---|---|
| 3 | gtggaagtacaagaaactgtt | 404 |
| 4 | atgttattgaggacgttgtta | 504 |
| 5 | atggaagaagcagatgtgtct | 551 |
| 6 | tacttcagcctcaatgtctat | 673 |
| 7 | cgggtgattctatacatgtgt | 711 |
| 8 | gtgtctgacgttggacatgtt | 728 |
| 9 | gacgttggacatgttggacat | 734 |
| 10 | tggacatgttggacatgttga | 748 |
| 11 | tagtggaagcagaaattgtca | 789 |
| 12 | gtggaagcagaaattgtcact | 791 |
| 13 | ttgtcactgatcctctgacta | 804 |
| 14 | accgacgtagtttcagaagaa | 824 |
| 15 | taccttatgatttccttggat | 938 |
| 16 | atggacacagagtcggaaatt | 1001 |
| 17 | gacacagagtcggaaattgat | 1004 |
| 18 | gagtcggaaattgatccttgt | 1010 |
| 19 | gtcggaaattgatccttgtaa | 1012 |
| 20 | gagagtgagcctgagaatgat | 1124 |
| 21 | agcaaatggatgacaatgaaa | 1341 |
| 22 | atggatgacaatgaaatcaaa | 1346 |
| 23 | ctgtgaatacgagacagctga | 1876 |
| 24 | taccaatgccagtactgcgaa | 2033 |
| 25 | gtcttctgactttctcggata | 2136 |
| 26 | taccaaagaggtgcagcaaca | 2155 |
| 27 | atgctcttatccaccaagaaa | 2175 |
| 28 | gcgaccacaagagttcgaact | 2220 |
| 29 | gaccacaagagttcgaactca | 2222 |
| 30 | accacaagagttcgaactcaa | 2223 |
| 31 | gtgatttgaaacgacacataa | 2244 |
| 32 | ttcagttcacacgaaagacta | 2266 |
| 33 | aagtgtgacatgtgtgataaa | 2294 |
| 34 | taggtgcaagagatgtagaaa | 2464 |
| 35 | aggcaacagagtgagcttaaa | 2492 |
| 36 | cacagtggcaggaaagtgtat | 2528 |
| 37 | cagtggcaggaaagtgtatca | 2530 |
| 38 | ggcaggaaagtgtatcagtgt | 2534 |
| 39 | aaccagcacataatgcgacat | 2681 |
| 40 | cagcacataatgcgacatcat | 2684 |

TABLE 1-continued siRNA target sequences of the human ZFX

| SEQ ID NO | Target Sequence | Start site |
|---|---|---|
| 41 | agcacataatgcgacatcata | 2685 |
| 42 | cacataatgcgacatcataaa | 2687 |

A double-stranded DNA oligonucleotide that contains sticky-ended Age I and EcoRI enzyme-cutting sites at both ends was synthesized for an siRNA target (e.g., SEQ ID NO:19) (Table 2). The Age I and EcoRI restriction cutting-enzymes were used on the pGCSIL-GFP vector (Shanghai Genechem Co., Ltd.; shown in FIG. 1) to linearize it; the restriction fragments were identified using agarose gel electrophoresis.

TABLE 2

Double-stranded DNA oligonucleotide that contains sticky-ended Age I and EcoRI enzyme-cutting sites at both ends

| No. | | 5' | Neck | Loop | Neck | 3' |
|---|---|---|---|---|---|---|
| 1 | Sense strand | CCGG | GTCGGAAATTG ATCCTTGTAA | TTCAAG AGA | TTACAAGGATC AATTTCCGAC | TTT TTG |
| | Anti-sense strand | AATTCA AAAA | GTCGGAAATT GATCCTTGTAA | TCTCTT GAA | TTACAAGGATC AATTTCCGAC | |

The vector DNAs, which had been linearized by double digestion, were joined to the purified double-stranded DNA oligonucleotide by means of T4 DNA ligase (restriction system as shown in Table 4, 37° C., reaction 1 h). Ligation occurred overnight in an appropriate buffer system (ligation system as shown in Table 5) at 16° C. and the ligation products were recovered. The ligation products were used to transform fresh E. coli competent cells that had been prepared with calcium chloride (for the transformation procedure, reference: *Molecular Cloning: A Laboratory Manual*, 2nd ed., supra at pp. 55-56). The bacterial clone surface grown from the ligation-transformation products was dissolved in 10 μl LB culture medium, mixed, and 1 μl was drawn as a template. General PCR primers (forward primer sequence: 5'-CCTATTTCCCATGATTCCTTCATA-3', as set forth in SEQ ID NO:44; reverse primer sequence: 5'-GTAATACGGTTATCCACGCG-3', as set forth in SEQ ID NO:45) upstream and downstream of the RNAi sequence in the lentiviral vector were designed. PCR identification tests (the PCR reaction system is as shown in Table 6-1; the reaction conditions are as shown in Table 6-2) were performed. Sequencing and sequence alignment analysis were performed on clones with positive PCR identifications. Correctly aligned clones were successfully constructed as RNAi vectors containing SEQ ID NO:19 and named as pGCSIL-GFP-ZFX-siRNA.

A pGCSIL-GFP-Scr-siRNA scrambled plasmid was constructed as negative control; the scrambled siRNA target sequence is 5'-TTCTCCGAACGTGTCACGT-3' (as set forth in SEQ ID NO:46). When the pGCSIL-GFP-Scr-siRNA scrambled plasmid was constructed, a double-stranded DNA oligonucleotide sequence that contains sticky-ended Age I and EcoRI enzyme-cutting sites at both ends was synthesized for the Scr siRNA target (Table 3). The remaining methods of construction and methods and conditions of identification were the same as for pGCSIL-GFP-ZFX-siRNA.

TABLE 3

A double-stranded DNA oligonucleotide that contains sticky-ended Age I and EcoRI enzyme-cutting sites at both ends

| No. | 5' | Neck | Loop | Neck | 3' |
|---|---|---|---|---|---|
| Sense strand | CCGG | TTCTCCGAACG TGTCACGT | TTCAAG AGA | ACGTGACACG TTCGGAGAA | TTT TTG |
| Anti-sense strand | AATTC AAAAA | TTCTCCGAACG TGTCACGT | TCTCTT GAA | ACGTGACACG TTCGGAGAA | |

T4 DNA ligase was used on vector linearized by double digestion (restriction system is shown in Table 4, 37° C., reaction 1 h).

TABLE 4 pGCSIL-GFP plasmid restriction system

| Reagent | Volume (µl) |
|---|---|
| pGCSIL-GFP plasmid (1 µg/µl) | 2.0 |
| 10 × buffer | 5.0 |
| 100 × BSA | 0.5 |
| Age I (10 U/µl) | 1.0 |
| EcoR I (10 U/µl) | 1.0 |
| dd H$_2$O | 40.5 |
| Total | 50.0 |

TABLE 5

Ligation system for vector DNA and double-stranded DNA oligonucleotide

| Reagent | Positive control (µl) | Self-ligation control (µl) | Ligation group (µl) |
|---|---|---|---|
| Linearized vector DNA (100 ng/µl) | 1.0 | 1.0 | 1.0 |
| Annealed double-stranded DNA Oligo (100 ng/µl) | 1.0 | — | 1.0 |
| 10 × T4 bacteriophage DNA ligase buffer solution | 1.0 | 1.0 | 1.0 |
| T4 bacteriophage DNA ligase | 1.0 | 1.0 | 1.0 |
| dd H$_2$O | 16.0 | 17.0 | 16.0 |
| Total | 20.0 | 20.0 | 20.0 |

TABLE 6-1

PCR Reaction System

| Reagent | Volume (µl) |
|---|---|
| 10 × buffer | 2.0 |
| dNTPs (2.5 mM) | 0.8 |
| Forward primer | 0.4 |
| Reverse primer | 0.4 |
| Taq polymerase | 0.2 |
| Template | 1.0 |
| ddH$_2$O | 15.2 |
| Total | 20.0 |

TABLE 6-2

| PCR reaction system procedure settings | | | | |
|---|---|---|---|---|
| 1 Cycle | 30 Cycles | | | 1 Cycle |
| 94° C. | 94° C. | 55° C. | 72° C. | 72° C. |
| 30 sec | 30 sec | 30 sec | 30 sec | 6 min |

2. Packaging ZFX-siRNA Lentiviruses

The DNA of the RNAi plasmid pGCSIL-GFP-ZFX-siRNA was extracted using Qiagen's plasmid extraction reagent kit and was used to prepare 100 ng/µl storage solution. 24 hours prior to transfection, pancreatic enzyme digestion was performed on human embryo kidney 293T cells in the logarithmic growth phase. Using DMEM complete culture medium containing 10% fetal bovine serum, the cell density was adjusted to $1.5 \times 10^5$ cells/ml; cells were inoculated onto a 6-well plate at 37° C. and cultivate in a 5% CO$_2$ culture box. It was used for transfection as soon as cell density reached 70%-80%. Two hours prior to transfection, the original culture medium was removed, and 1.5 ml fresh, complete culture medium was added. In accordance with the instructions for Sigma-Aldrich's MISSION Lentiviral Packaging Mix™ reagent kit, Packing Mix (PVM) 20 µl, PEI 12 µl, and serum-free DMEM culture 400 µl were added. 20 µl of the above-described extracted plasmid DNA was added to the above-described PVM/PEI/DMEM mixture. The above-described transfection mixture and materials were incubated at room temperature for 15 minutes, and transferred into a culture medium of human embryo kidney 293T cells, and culture at 37° C. in a 5% CO$_2$ culture box for 16 hours. The culture medium containing the transfection mixture and materials was discarded, the cells were washed with PBS solution, and added with complete culture medium 2 ml, and cultured for 48 hours. The cell supernatant fluid was collected, purified with a Centricon Plus-20™ centrifugal filter (Millipore), and the lentiviruses were concentrated. The following steps were performed: (1) 4° C., centrifuge at 4,000 g for 10 min, and remove cell debris; (2) filter supernatant with 0.45 µm filter in a 40 ml ultrafast centrifuge tube; (3) centrifuge at 4,000 g for 10-15 min until the desired volume of viral concentrate is reached; (4) after centrifuging ends, separate the filtration cup and the cup for collecting filtrate, turn the filtration cup upside down onto the sample collection cup, centrifuge for 2 min, keeping centrifugal force at a maximum of 1,000 g; (5) remove the centrifuge cup from the sample collection cup. The sample collection contained viral concentrate. After packing the viral concentrate in separate containers, it was stored at −80° C. The siRNA sequence contained in the viral concentrate was SEQ ID NO:43. The packaging process for the control lentiviruses was the same as for the ZFX-siRNA lentiviruses, except that pGCSIL-GFP-Scr-siRNA vectors were substituted for pGCSIL-GFP-ZFX-siRNA vectors.

EXAMPLE 2

ZFX Gene Silencing Efficiency as Measured by Quantitative Real-Time PCR

Pancreatic enzyme digestion was performed on log-phase human larynx cancer Hep 2 cells, lung cancer 95D cells, stomach cancer AGS cells, liver cancer SMMC-7721 cells, breast cancer MCF-7 cells, and glioma U251 cells to prepare a cellular suspension (cell count of roughly $5 \times 10^4$/ml); cells were inoculated into a 6-well plate, and cultivated until a cell confluency of approximately 30% was reached. In accordance with the multiplicity of infection value (MOI, Hep2:

10, 95D: 2, AGS: 100, SMMC-7721: 20, MCF-7: 20, U251: 10), a suitable quantity of viruses prepared according to Example 1 was added. After culturing for 24 h, the culture medium was replaced. Cells were collected after 5 days of infection. Total RNA was extracted in accordance with Invitrogen's Trizol™ operating manual. cDNA was produced by reverse transcription of RNA in accordance with Promega's M-MLV™ operating manual (for the reverse transcription reaction system, see Table 7, 42° C. reaction 1 hour, followed by bathing 10 min at 70° C. in a water bath to deactivate the reverse transcriptase).

A TP800™ real time PCR instrument (TAKARA) was used to conduct real-time quantitative measurement. The ZFX gene primers were as follows: forward primer 5'-GGCAGTCCACAGCAAGAAC-3' (SEQ ID NO: 47) and reverse primer 5'-TTGGTATCCGAGAAAGTCA-GAAG-3' (SEQ ID NO: 48). Using the housekeeping gene GAPDH as an internal reference, the primer sequence was as follows: forward primer 5'-TGACTTCAACAGCGA-CACCCA-3' (SEQ ID NO: 49) and reverse primer 5'-CAC-CCTGTTGCTGTAGCCAAA-3' (SEQ ID NO: 50). The reaction system was configured according to the proportions in Table 8.

TABLE 7

Reverse transcription reaction system

| Reagent | Volume (μl) |
|---|---|
| 5 × RT buffer | 4.0 |
| 10 mM dNTPs | 2.0 |
| RNasin | 0.5 |
| M-MLV-RTase | 1.0 |
| DEPC H$_2$O | 3.5 |
| Total | 11.0 |

TABLE 8

Real-time PCR reaction system

| Reagent | Volume (μl) |
|---|---|
| SYBR premix ex taq | 10.0 |
| Forward primer (2.5 μM) | 0.5 |
| Reverse primer (2.5 μM) | 0.5 |
| cDNA | 1.0 |
| ddH$_2$O | 8.0 |
| Total | 20.0 |

Figure 2:
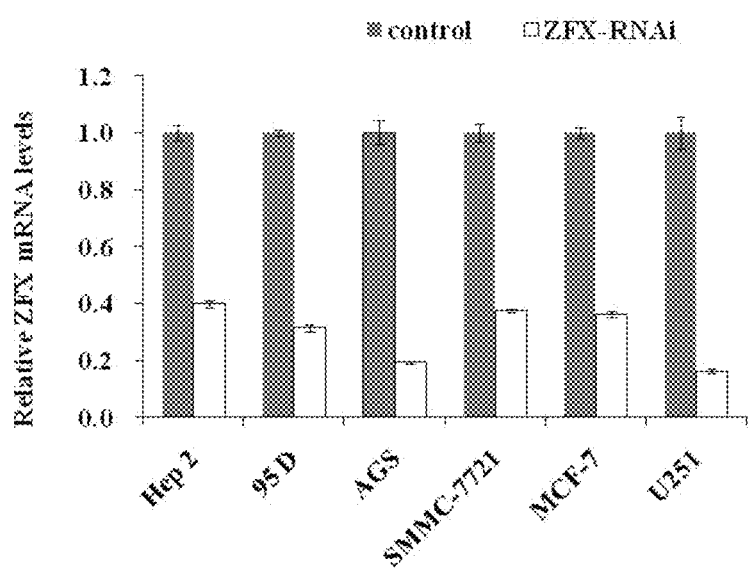
FIG. 2 shows significantly decreased ZFX mRNA expression level 5 days after ZFX-RNAi lentiviruses infection of human larynx cancer Hep 2 cells, lung cancer 95D cells, stomach cancer AGS cells, liver cancer SMMC-7721 cells, breast cancer MCF-7 cells, and glioma U251 cells.
Figure 3:
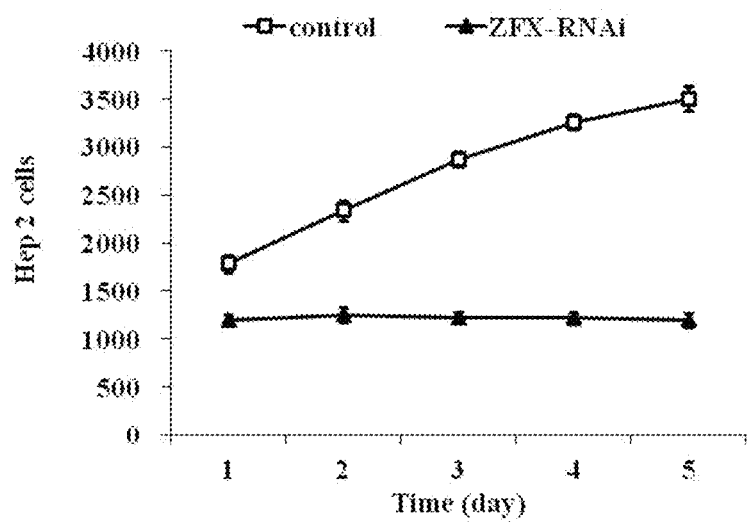
FIG. 3 shows that, 5 days after infecting human larynx cancer Hep 2 cells, ZFX-RNAi lentiviruses cause inhibition of cell proliferation.
Figure 4:
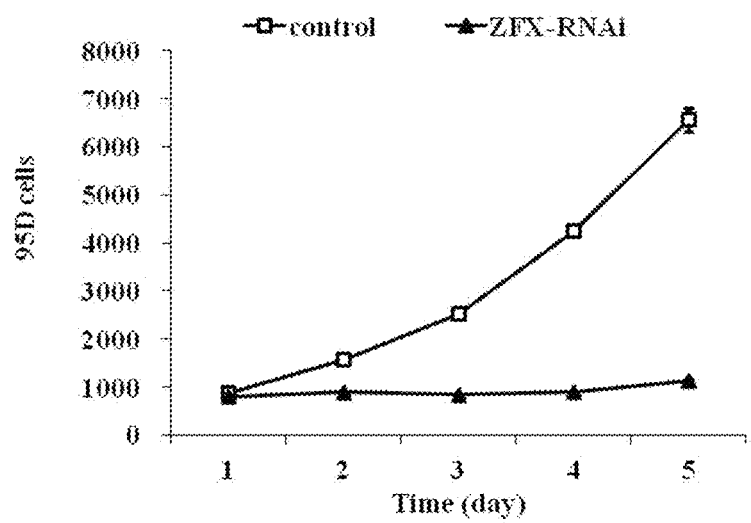
FIG. 4 shows that, 5 days after infecting human lung cancer 95D cells, ZFX-RNAi lentiviruses cause inhibition of cell proliferation.
Figure 5:
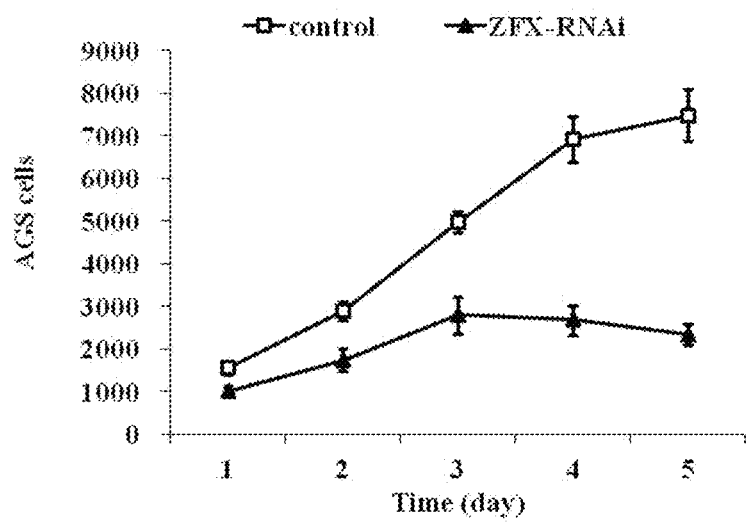
FIG. 5 shows that, 5 days after infecting human stomach cancer AGS cells, ZFX-RNAi lentiviruses cause inhibition of cell proliferation.
Figure 6:
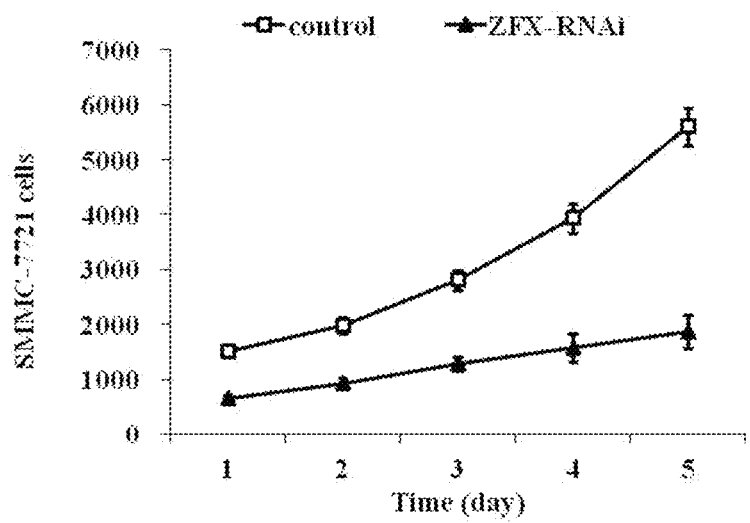
FIG. 6 shows that, 5 days after infecting human liver cancer SMMC-7721 cells, ZFX-RNAi lentiviruses cause inhibition of cell proliferation.
Figure 7:
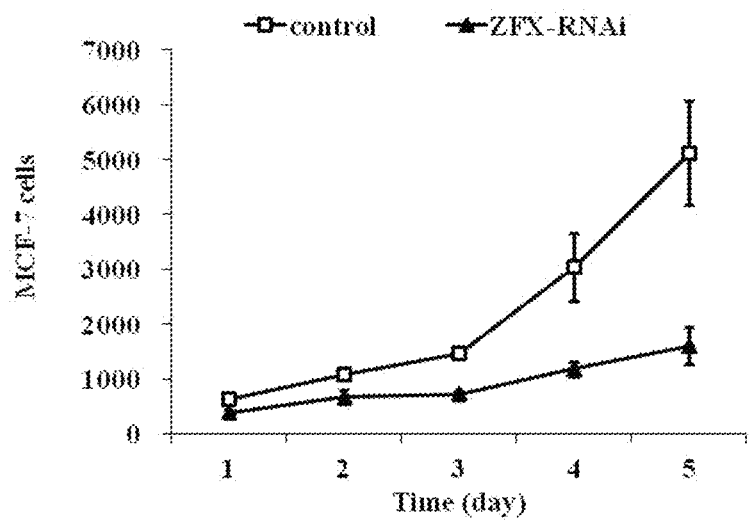
FIG. 7 shows that, 5 days after infecting human breast cancer MCF-7 cells, ZFX-RNAi lentiviruses cause inhibition of cell proliferation.
Figure 8:
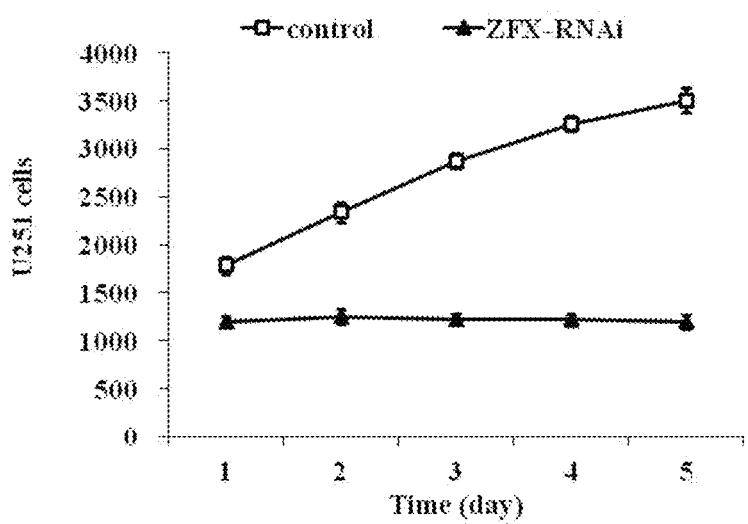
FIG. 8 shows that, 5 days after infecting human glioma U251 cells, ZFX-RNAi lentiviruses cause inhibition of cell proliferation.

The procedure to two-step real-time PCR was set as follows: pre-denaturation 95° C., 15 s; thereafter, each step denaturation at 95° C., 5 s; annealing extension 60° C., 30 s; total of 45 cycles. The absorbance value in each extension phase was read. PCR was followed by denaturation at 95° C. for 1 min; then cooled to 55° C. for annealing. Temperature was changed in increments of 0.5° C. from 55° C. to 95° C., maintaining for 4 s. At the same time, absorbance readings were taken and produce a melting curve was produced. The $2^{-\Delta\Delta Ct}$ analytic method was used to calculate the expression abundance of infected ZFX mRNA. Cells infected with the control virus (Lv-Scr-siRNA) served as a control. Test results show that the expression of ZFX mRNA in human Hep 2 cells, lung cancer 95D cells, stomach cancer AGS cells, liver cancer SMMC-7721 cells, breast cancer MCF-7 cells, and glioma U251 cells dropped 60.2%, 68.5%, 80.8%, 62.6%, 63.7%, and 83.9%, respectively (FIG. 2).

EXAMPLE 3

Measurement of the Proliferation Capacity of Tumor Cells Infected with ZFX-siRNA Lentivirus Pancreatic enzyme digestion was performed on log-phase human larynx cancer Hep 2 cells, lung cancer 95D cells, stomach cancer AGS cells, liver cancer SMMC-7721 cells, breast cancer MCF-7 cells, and glioma U251 cells to prepare a cellular suspension (cell count of roughly $5 \times 10^4$/ml). The cells were inoculated into a 6-well plate, and cultivated until a cell confluency of approximately 30% is reached. In accordance with the multiplicity of infection value (MOI, Hep2: 10, 95D: 2, AGS: 100, SMMC-7721: 20, MCF-7: 20, U251: 10), a suitable quantity of viruses was added. After culturing for 24 hours, the culture medium was replaced. After 5 days of infection time, cells were collected from each test group while in the logarithmic growth phase. The cells were resuspended in complete culture medium to form a cell suspension ($2 \times 10^4$/ml) and inoculated in a 96-well plate at a cell density of 2,000/well. Each group was repeated in 5 wells, with 100 μl per well. After filling the plate, the cells were cultured in a 5% CO$_2$ culture box set at 37° C. Beginning on the second day after filling the plate, the plate was read once daily using a Cellomics™ (Thermo Fisher) device for five consecutive days. By adjusting the input parameters of the Cellomics™ ArrayScan, the enhanced green fluorescent cell count per plate scan was calculated. The data were used to plot a statistical graph and cell proliferation curve (shown in FIGS. 3-8). The results indicate that, five days after in vitro culturing of each group of lentivirus-infected tumor cells, proliferation rates decreased significantly, far below the proliferation rates of the tumor cells in the control groups.

EXAMPLE 4

Testing ZFX Gene Overexpression in Tumor Cells

Tissue samples used were from human pancreatic cancer, breast cancer, colorectal cancer, lung cancer, and stomach cancer, and from paracancerous regions of the above-described cancers.

ZFX antibody: from Sigma™.

Figure 9:
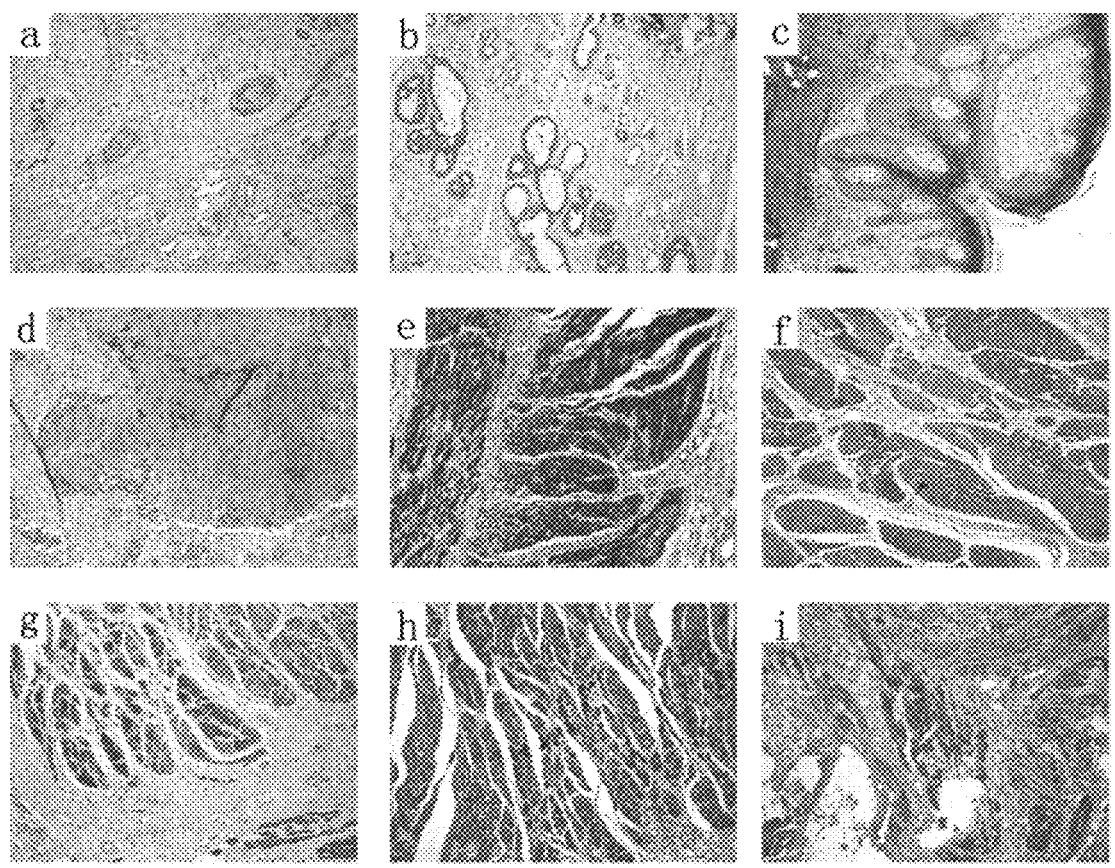
FIG. 9 shows immunohistochemical staining using anti-ZFX antibodies on human tumor tissues: a. pancreatic cancer; b. breast cancer; c. colorectal cancer; d, e: lung cancer; f, g, h, i: stomach cancer.
Figure 10:
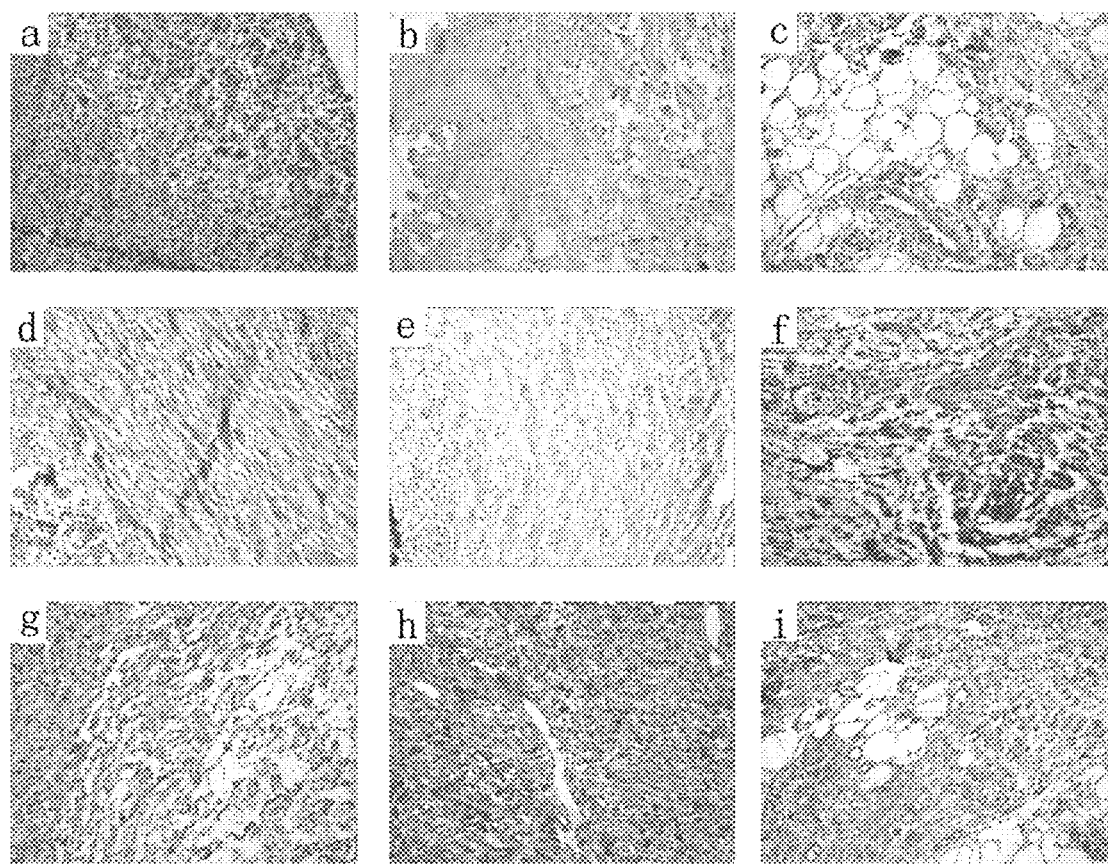
FIG. 10 shows immunohistochemical staining using anti-ZFX antibodies on human paracancerous tissues: a. pancreatic cancer; b. breast cancer; c. colorectal cancer; d, e: lung cancer; f, g, h, i: stomach cancer.

Test Method:

A tissue microarray was put in a 60° C. incubator and heated for 30 minutes. Then the tissue microarray was dewaxed. The dewaxing process was as follows: dimethyl benzene 15 minutes; soak 10 minutes in sequence: in dimethyl benzene:ethanol=1:1 mixture, in absolute alcohol, in 95% ethanol, in 85% ethanol, in 75% ethanol, and in distilled water; then use distilled water or PBS to prepare fresh 3% H$_2$O$_2$, and seal for 10 minutes at room temperature. For antigen retrieval, 0.01 M sodium citrate buffer solution (pH 6.0) was heated on high heat until it boiled; then the tissue microarray was placed in the solution and heated for 20 minutes on low heat. After cooling naturally to room temperature, the tissue microarray was set in distilled water and soaked for 10 minutes; sealed with 10% serum (TB S preparation) for 30 minutes; aspirated, and without washing, ZFX antibody (1:100 dilution) was added and incubated overnight. The tissue microarray was washed with TBS twice, each time for 5 minutes; HRP-labeled goat anti-rabbit secondary antibodies were added and incubated at room temperature for 60 minutes; washed with TBS four times, each time for 5 minutes. DAB dye was added until light yellow appeared. The tissue microarray was placed in distilled water to terminate reaction; soaked in hematoxylin for 30 seconds; rinsed with clear water 7 or 8 times; dehydrated and mounted; soaked 5 minutes in sequence: 75% ethanol, 85% ethanol, 95% ethanol, absolute ethanol, dimethyl benzene:ethanol=1:1 mixture, and dimethyl benzene. The tissue microarray was dipped 30 ul onto neutral plastic and mounted with cover glass, dried by airing, and observed and photographed (results shown in FIGS. 9 and 10).

The results indicate:

ZFX antibodies were used to conduct immunohistochemical expression tests on different tumor tissues. The results show high expression of ZFX gene-coded proteins in human pancreatic cancer, breast cancer, colorectal cancer, lung cancer and stomach cancer tissue samples (FIG. 9, brown color represents positive expression).

ZFX antibodies were used to conduct immunohistochemical expression tests on the paracancerous regions of different tumor tissues. The results show no expression of ZFX proteins in the paracancerous regions of human pancreatic cancer, breast cancer, colorectal cancer, lung cancer and stomach cancer tissue samples. This indicates that ZFX is in a non-expressive mode in paracancerous tissues. Therefore, based on the results of this experiment, that ZFX gene expression can be used for the diagnosis of cancer.

EXAMPLE 5

In Vivo Tumorigenic Ability Experiment Result of Lentivirus-Infected Tumor Cells by ZFX-siRNA Lentivirus Pancreatic enzyme digestion was performed on log-phase human stomach cancer SGC7901 cells to prepare a cellular suspension (cell count of roughly $5 \times 10^4$/ml). The cells were inoculated into a 6-well plate, and cultivated until a cell count of approximately 30% is reached. In accordance with the multiplicity of infection value (MOI: 10), a suitable quantity of viruses was added. After culturing for 24 hours, the culture medium was replaced. After 5 days of infection time, cells from each test group and cells from the control groups while both in the logarithmic growth phase, were collected respectively. The cells were resuspended in complete culture medium to form a cell suspension which is injected into the right armpit of 5 to 6 weeks old female BALB/c nude mice ($2 \times 10^6$ cells per mouse). SGC7901 cells infected with ZFX-siRNA lentivirus is injected into the mice of the test group, while SGC7901 cells infected with Lv-Scr-siRNA lentivirus is injected into the mice of the control group. Each group included five nude mice.

Figure 11:
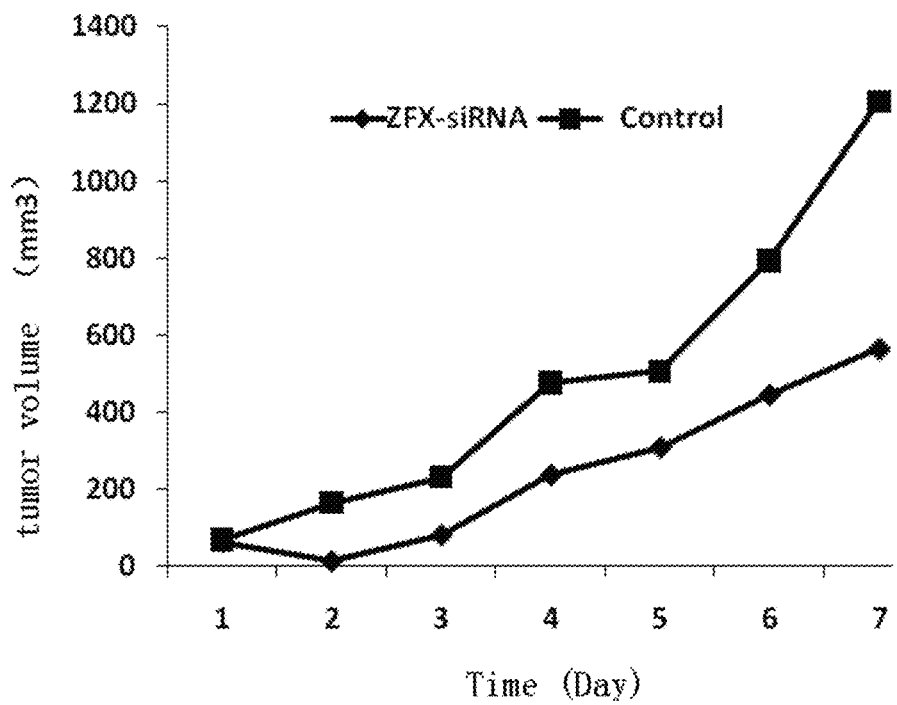
FIG. 11 shows in vivo tumorigenic ability experiment result of tumor cells infected by ZFX-siRNA lentiviruses; a. tumor cell growth curve; b. in vivo fluorescence detection result of tumor in nude mice.
Figure 11:
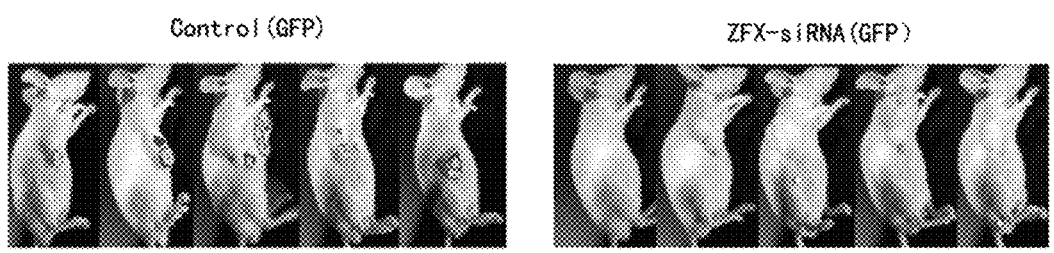

After the injection, the nude mice were fed until visiable tumor appeared (about one week), and the size and diameter of tumors were observed and measured by NightOWL II983 spectroscopic in vivo imaging system (Berthold Technologies) and tumor cell growth curve was drawn as shown in FIG. 11*a*. After seven-day consecutive observation, the in vivo image of tumors in the mice was obtained as shown in FIG. 11*b*. It was observed that the tumorigenic ability of the test group was much lower than that of the control group. According to such result, it was indicated that ZFX-siRNA could inhibit the proliferation of in vivo tumors.

We claim:

1. A method for inhibiting or attenuating the growth, proliferation, and/or survival of a tumor cell, which method comprises administering to the tumor cell a nucleic acid that specifically inhibits transcription or translation of a zinc finger protein X-linked (ZFX) gene, or expression of the ZFX protein, thereby inhibiting the growth, proliferation, and/or survival of the tumor cell.

2. The method of claim 1, wherein the nucleic acid comprises an antisense oligonucleotide, a double stranded RNA (dsRNA), a ribozyme, an RNase III-prepared short interfering RNA (esiRNA) or a vector-expressed short hairpin RNAs (shRNA).

3. The method of claim 2, wherein the dsRNA, ribozyme, esiRNA or shRNA comprises a subsequence of a promoter of the ZFX gene or a subsequence of the ZFX gene.

4. The method of claim 3, wherein the dsRNA is an siRNA.

5. The method of claim 4, wherein the siRNA comprises a sense strand, which comprises a nucleotide sequence substantially identical to a target sequence in the ZFX gene, and an antisense strand, wherein the sense and antisense strands form an RNA duplex.

6. The method of claim 1, wherein the ZFX gene is from human.

7. The method of claim 5, wherein the target sequence in the ZFX gene comprises a sequence set forth in SEQ ID NOs: 1-42.

8. The method of claim 1, wherein the tumor is selected from the group consisting of laryngeal cancer, lung cancer, stomach cancer, liver cancer, mammary gland cancer and glioma.

9. The method of claim 1, wherein the growth of the tumor cell is associated with the expression of the ZFX protein.

10. The method of claim 1, wherein the nucleic acid is administered at a level sufficient to lower the transcription or translation of the ZFX gene, or the expression of the ZFX protein.

11. The method of claim 10, wherein the expression of the ZFX gene is attenuated by at least about 50%, 80%, 90%, 95% or 99%.

12. The method of claim 1, wherein the nucleic acid comprises an oligonucleotide that attenuates the expression of the ZFX gene in the tumor cell, which oligonucleotide comprises:
   a) a dsRNA sequence comprising a nucleotide sequence that hybridizes under stringent conditions to the ZFX gene; or
   b) a DNA sequence comprising a nucleotide sequence that is transcribed in the tumor cell to an shRNA comprising a nucleotide sequence that hybridizes under stringent conditions to the ZFX gene.

13. The method of claim 12, wherein a first strand of the dsRNA is substantially identical to about 15-27 consecutive nucleotides of the ZFX gene, and a second strand of the dsRNA is substantially complementary to the first strand.

14. The method of claim 12, wherein a first strand of the dsRNA is substantially identical to a target sequence in the ZFX gene.

15. The method of claim 12, wherein the ZFX gene is from human.

16. The method of claim 12, wherein the ZFX gene comprises a sequence set forth in SEQ ID NO: 1.

17. The method of claim 14, wherein the target sequence in the ZFX gene comprises a sequence set forth in SEQ ID NOs: 1-42.

18. The method of claim 12, wherein the shRNA comprises a sense fragment, which comprises a nucleotide sequence substantially identical to a target sequence in the ZFX gene, and an antisense fragment, wherein the sense and antisense fragments are separated by a loop fragment.

19. The method of claim 18, wherein the loop fragments comprises a sequence selected from the group consisting of UUCAAGAGA, AUG, CCC, UUCG, CCACC, CTCGAG, AAGCUU and CCACACC.

20. The method of claim 19, wherein the shRNA comprises the sequence set forth in SEQ ID NO: 43.

21. The method of claim 1, wherein the nucleic acid comprises a lentivirus vector comprising a DNA sequence comprising a nucleotide sequence that is transcribed in the tumor cell to an shRNA comprising a nucleotide sequence that hybridizes under stringent conditions to the ZFX gene,
   wherein the shRNA comprises a sense fragment, which comprises a nucleotide sequence substantially identical to a target sequence in the ZFX gene, and an antisense fragment, wherein the sense and antisense fragments are separated by a loop fragment.

22. The method of claim 21, wherein the lentivirus vector further comprises a promoter sequence.

23. The method of claim 21, wherein the lentivirus vector further comprises a nucleotide sequence encoding a detectable marker in the tumor cell.

24. The method of claim 23, wherein the detectable marker is a green fluorescent protein (GFP).

25. The method of claim 21, wherein the lentivirus vector is selected from the group consisting of pLKO.1-puro, pLKO.1-CMV-tGFP, pLKO.1-puro-CMV-tGFP, pLKO.1-CMV-Neo, pLKO.1-Neo, pLKO.1-Neo-CMV-tGFP, pLKO.1-puro-CMV-TagCFP, pLKO.1-puro-CMV-TagYFP, pLKO.1-puro-CMV-TagRFP, pLKO.1-puro-CMV-TagFP635, pLKO.1-puro-UbC-TurboGFP, pLKO.1-puro-UbC-TagFP635, pLKO-puro-IPTG-1xLacO, pLKO-puro-IPTG-3xLacO, pLP1, pLP2, pLP/VSV-G, pENTR/U6, pLenti6/BLOCK-iT-DEST, pLenti6-GW/U6-laminshrna, pcDNA1.2/V5-GW/lacZ, pLenti6.2/N-Lumio/V5-DEST, pGCSIL-GFP and pLenti6.2/N-Lumio/V5-GW/lacZ.

26. A method for treating tumor in a subject, which method comprises administering an effective amount of a pharmaceutical composition to the subject, wherein the pharmaceutical composition comprises an oligonucleotide that attenuates the expression of a zinc finger protein X-linked (ZFX) gene in a tumor cell, which oligonucleotide comprises:
   a) a dsRNA sequence comprising a nucleotide sequence that hybridizes under stringent conditions to the ZFX gene; or
   b) a DNA sequence comprising a nucleotide sequence that is transcribed in the tumor cell to an shRNA comprising a nucleotide sequence that hybridizes under stringent conditions to the ZFX gene.

27. The method of claim 1, wherein the nucleic acid comprises a fragment of the ZFX gene, wherein the nucleic acid is not the full-length nucleotide sequence of the ZFX gene.

* * * * *